United States Patent [19]

Blackman

[11] Patent Number: 4,466,426
[45] Date of Patent: Aug. 21, 1984

[54] SYRINGE WITH ACTINIC RAY BLOCKING STRIPE

[76] Inventor: Seymour N. Blackman, c/o Premo Pharmaceutical Laboratories, Inc., 111 Leuning St., South Hackensack, N.J. 07606

[21] Appl. No.: 485,956

[22] Filed: Jun. 13, 1983

Related U.S. Application Data

[63] Continuation of Ser. No. 278,593, Jun. 29, 1981, abandoned.

[51] Int. Cl.³ .............................................. A61M 5/00
[52] U.S. Cl. ...................................... 128/1.1; 604/210
[58] Field of Search .............. 604/209, 210, 211, 187, 604/232, 207, 208; 128/1.1

[56] References Cited

U.S. PATENT DOCUMENTS

| | | | |
|---|---|---|---|
| 2,474,496 | 6/1949 | Rayman | 604/210 |
| 2,764,981 | 10/1956 | Helmer | 604/210 |
| 2,875,761 | 3/1959 | Helmer | 604/210 |
| 3,769,490 | 10/1973 | Czaplinski | 128/1.1 |
| 3,831,602 | 8/1974 | Broadwin | 604/210 |
| 4,048,997 | 9/1977 | Raghavachari et al. | 128/1.1 |
| 4,050,459 | 9/1977 | Sanchez | 604/210 |
| 4,063,662 | 12/1977 | Drummond et al. | 604/210 |
| 4,148,315 | 4/1979 | Berezkin et al. | 604/210 |

Primary Examiner—John D. Yasko
Attorney, Agent, or Firm—Kirschstein, Kirschstein, Ottinger & Israel

[57] ABSTRACT

A hypodermic syringe which in one form has a barrel transparent to actinic rays, plus an imperforate rectilinear strip for selectively blocking actinic rays in order to protect labile liquid medication in the syringe. The syringe plunger has an arrangement that provides tactile and audible indications of different positions of the plunger in the barrel. In another form, a similar arrangement assists persons with failing vision.

21 Claims, 10 Drawing Figures

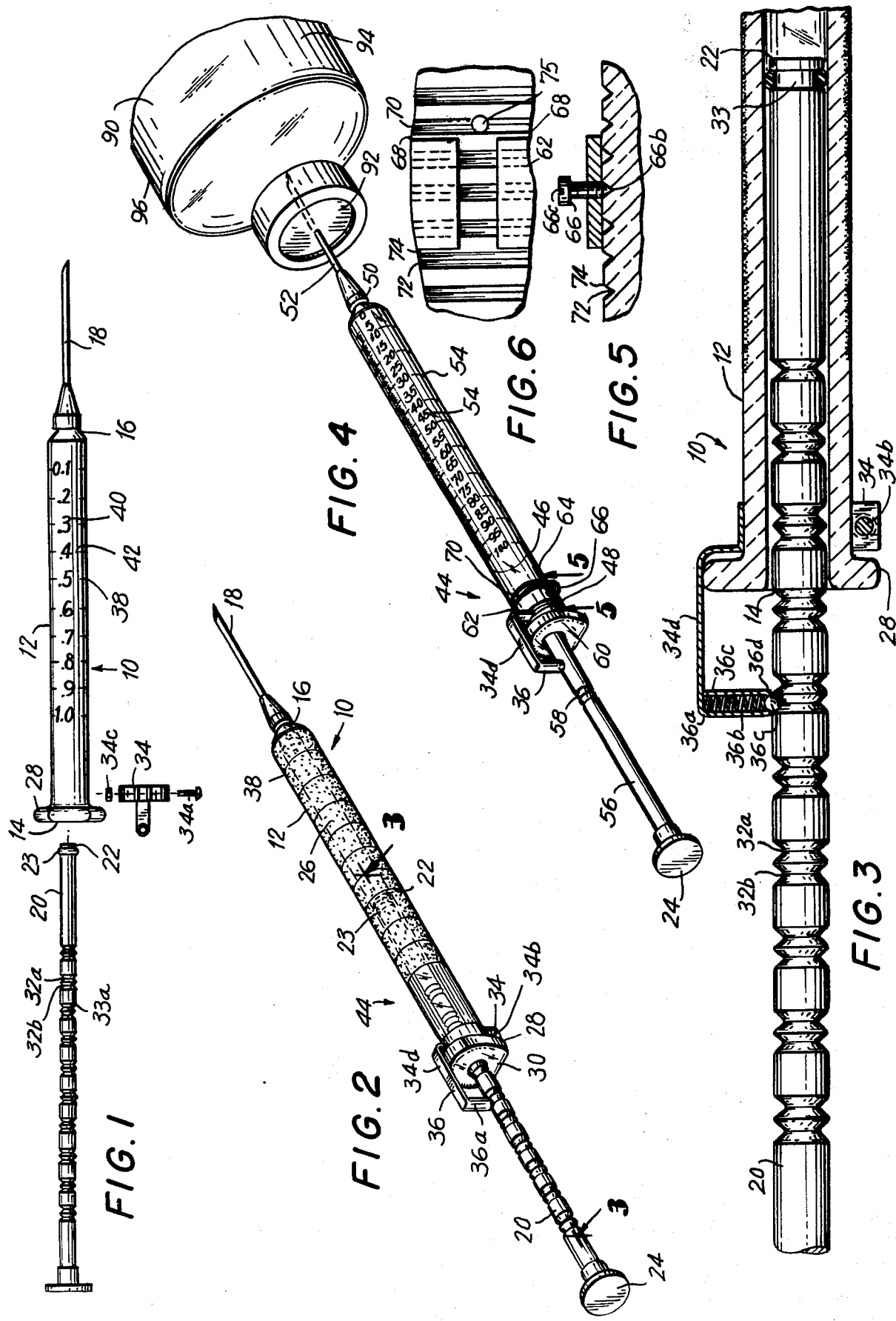

SYRINGE WITH ACTINIC RAY BLOCKING STRIPE

This is a continuation of application Ser. No. 278,593 filed June 29, 1981, now abandoned.

BACKGROUND OF THE INVENTION

1. Field of the Invention

The present invention generally relates to a hypodermic syringe and a method for inoculating large numbers of people with medication which is adversely affected by actinic rays and, more particularly, to a hypodermic syringe which contains an imperforate opaque rectilinear strip on its transparent medicament-preloaded barrel, at least one annular groove on a plunger of the syringe and a method for using the syringe to inoculate large numbers of people. Another aspect of the invention relates to a method utilizing the syringe to inject diabetics.

2. Description of the Prior Art

It is recognized that there are certain medications which are labile to actinic rays. That is to say, the effectiveness of these medications is weakened or destroyed by exposure to sunlight. One example of such a medication is a BCG vaccine which provides active immunity against tuberculosis. Since inoculation of large numbers of people frequently is done out of doors in the sunlight, this creates a problem. The degradation of medication is particularly bad where, as in the case of mass inoculations, there are a large number of preloaded syringes lying out in the sunlight. It is thus important to provide a hypodermic syringe which protects its contents from degradation by actinic rays.

Further, when inoculating large segments of the population, it is economical and expeditious to have a syringe which includes enough medication for multiple individual doses. In such a system it is important to have quick and accurate means for proper individual dosage reading and dispensation.

It has also been recognized when medication is drawn out of a vial with an air impervious seal, that the air pressure in the vial lowers. As more and more medication is drawn out, a vacuum is created which makes it increasingly difficult to aspirate the medication from the vial and into the hypodermic syringe.

Various modifications to the standard hypodermic syringe have been attempted in the prior art. Of particular interest herein are the following:

U.S. Pat. No. 3,885,562 discloses a hypodermic syringe which has flats on its finger flange, the flats so positioned as to force a marking surface on the syringe into a visible position. Although the syringe of this invention is successful in what it attempts to do, it has no utility in protecting medication labile to actinic rays from those rays.

U.S. Pat. No. 4,048,997 discloses a hypodermic syringe with a separate sheet of thin resin film for blocking actinic rays. The film sheet covers the entire girth of the syringe barrel and is removable therefrom for inspection of the syringe contents at the time of dispensation of medication. The construction of the sheet in this manner slows down the process of inoculating individuals, due to the necessity of removing the protective sheet prior to said dispensation of medication. Further, such an arrangement creates difficulties if the syringe is to contain multiple doses, as the protective sheet must continuously be removed and replaced.

U.S. Pat. Nos. 3,596,659; 3,973,554; 4,062,353; and 4,185,619 all disclose hypodermic syringes with some type of associated device to reduce the transmission of radiation. All of these utilize removable shield portions which must be taken off of the syringe and replaced thereon. These devices have no application to protecting medication which is labile to actinic rays.

SUMMARY OF THE INVENTION

1. Purposes of the Invention

Accordingly, it is an object of the invention to provide a hypodermic syringe, and method of inoculating large numbers of people with liquid medication adversely affected by actinic rays, which avoid the disadvantages of the prior art syringes.

It is another object of the invention to construct a hypodermic syringe, with an imperforate ray blocking means which does not have to be removed from the syringe prior to the dispensation of medication.

It is still another object of the invention to construct a hypodermic syringe of the character described which is constantly oriented in a manner such that the ray blocking means is uppermost.

It is yet a further object of the invention to provide a method for mass inoculations with medications labile to actinic rays.

Another object of the invention is to provide easily and accurately readable visual indicia means.

Still another object of the invention is to provide an auditory and tactile indication of the position of a plunger in the syringe when aspirating, and upon completion of an individual injection.

Yet another object of this invention is to provide a method of safely and accurately injecting diabetics with insulin.

Another object of the invention is to facilitate a method of drawing medication out of vials with air impermeable seals without creating vacuums in said vials.

Other objects of the invention in part will be obvious and in part will be pointed out hereinafter.

2. Features of the Invention

In keeping with these objects, and others which will become apparent hereinafter, one feature of the invention, resides, briefly stated, in a hypodermic syringe whose contents are adversely affected by actinic rays, which contains as an integral part of the syringe an imperforate, rectilinear means for blocking actinic rays.

In a preferred embodiment, the means for blocking actinic rays consists of an applied band on a segment of the barrel of the hypodermic syringe, the segment covering a large enough portion of the barrel and being so situated as to afford protection from the actinic rays to the barrel contents. A method of obtaining such band is to screen a ceramic or a non-transparent glass frit or a metallic stain-producing paste on the barrel and then bake it. The band of a ceramic frit desirably is a light color. If a metallic stain is used it should be dark colored.

Further, in accordance with another feature of the invention, the hypodermic syringe contains thereon means for constantly orienting the ray blocking means upwardly.

Another feature of the invention resides in the fact that, in the preferred embodiment there are cooperating visual indicia means on the syringe and the plunger for indicating the position of the plunger in the barrel. The indicia means are such that they contrast in color to the ray blocking means thereby aiding the user in easily and accurately reading the plunger's position. The indicia means is such as to contrast with the actinic ray blocking band against which it is viewed.

A further safety feature of this invention is embodied in the provision of auditory and tactile indicia means for indicating the position of the plunger in the barrel.

As noted above, in its preferred embodiment, the syringe contains a means for blocking actinic rays and a means for constantly orienting the ray blocking means upwardly. In combination these two features assist in mass inoculation with medications labile to actinic rays.

The provision of auditory and tactile indicia means further provides a time saving adjunct for mass inoculations and a method of safely and accurately injecting diabetics with insulin of a desired volume and facilitating withdrawal of medication out of vials sealed with air impermeable seals without creating vacuums in these vials.

The novel features which are considered as characteristic of the invention are set forth in particular in the appended claims. The invention itself, however, both as to its construction and method of operation, together with additional objects and advantages thereof, will best be understood from the following description of specific embodiments when read in connection with the accompanying drawings.

BRIEF DESCRIPTION OF THE DRAWINGS

FIG. 1 is an exploded view of the hypodermic syringe in accordance with the present invention;

FIG. 2 is a perspective view of the hypodermic syringe of FIG. 1;

FIG. 3 is an enlarged sectional view as taken substantially along line 3—3 of FIG. 2;

FIG. 4 is a perspective view of another embodiment of the present invention being used with a medication vial sealed with an air impermeable seal in accordance with one of the methods of the invention;

FIG. 5 is an enlarged sectional view as taken substantially along line 5—5 of FIG. 4;

FIG. 6 is an enlarged view of the fine adjustment means and the series of divisional means and divisional lines of the barrel and clip portions of FIG. 5;

DETAILED DESCRIPTION OF THE PREFERRED EMBODIMENTS

Figure 7:
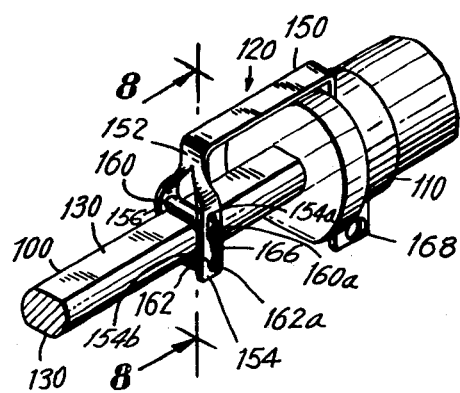
FIG. 7 is a partial broken away view of another embodiment of the plunger and clip portion of the invention.

Referring now in detail to the drawings, and more particularly to FIGS. 1 and 2, the reference numeral 10 denotes one embodiment of the hypodermic syringe of the present invention. The syringe 10 has a transparent, elongated barrel 12. The barrel 12 is, more specifically, transparent to actinic rays emanating from the sun. The barrel 12, contains medication, such as BCG vaccine, which is adversely affected by the afore-mentioned actinic rays.

The barrel 12 has two open ends 14 and 16. End 16 of the barrel 12 is shaped and dimensioned to detachably receive the hub of a metal hypodermic needle 18 which is shown fixed in place in the drawings.

A standard stainless steel needle or a platinum needle which can be repeatedly flame sterilized, may be utilized.

The barrel 12 is made of clear borosilicate glass, the standard material for hypodermic syringe barrels. The barrel contains visual indicia means comprising a series of circumferential lines 38 and associated numerical markings 40. The lines 38 and associated markings 40 will be discussed in further detail hereinafter.

A plunger 20 is insertable into the open end 14 of the barrel and mounted for sliding movement lengthwise of the barrel 12. The plunger 20 is an elongated metal rod and has a bottom end 22. The plunger is visible through the transparent barrel 12. The bottom end 22 is provided with a dark colored circumferential annular elastomeric ring 23 thereon that forms a sliding seal with the interior of the barrel. The annular ring 23 is visible through the barrel 12 and aids a user in locating the position of the bottom end of the plunger 20 in the barrel 12. When the leading edge of annular ring is in line with the appropriate circumferential line 38 and associated marking 40 the user can "read" the position of the plunger 20 in the barrel 12.

The plunger has a top manipulative handle 24 to assist the user in shifting the plunger lengthwise of the barrel. As thus far described the syringe is conventional.

As best shown in FIG. 2, the barrel 12 contains an imperforate rectilinear means 26 for blocking actinic rays. The ray blocking means extends generally the full length of the indicia marked portion of the barrel 12 and at least 150° circumferentially. The ray blocking means must extend at least 150° and preferably somewhat more, e.g. 190°, to prevent lateral penetration of the barrel by actinic rays. The ray blocking means is an integral part of the barrel 12 and is not removable.

As heretofore stated, the ray blocking means consists of an applied band on a segment of the barrel 12. A method of obtaining said band is to screen a ceramic or glass frit or a metallic stain-producing compound onto the barrel and then bake it. The band desirably is a light color and has a low transmissivity to actinic rays.

The barrel has an integral circular flange that extends outwardly of the barrel and is located proximate to the open end 14 thereof.

The flange 28 is formed with a single depressed flat portion 30 that provides a means for insuring that the barrel, when the syringe is lying on a flat supporting surface, e.g. a table top, is oriented so that the ray blocking means 26 faces upwardly. The flat portion 30 is located diametrically opposite to the longitudinal center of the ray blocking means. When the syringe 10 is in its proper orientation, the flat portion 30 is downward, in contact with the supporting surface, and the ray blocking means is uppermost. In this manner the contents of the syringe 10 is protected from exposure to the sun's actinic rays.

The plunger 20 is formed with at least two annular circumferential measuring grooves intermediate its ends. Measuring groove 32a is exemplificative of all possible annular circumferential grooves. Measuring groove 32a corresponds to a predetermined volume of medication between the bottom end of the plunger 22 and the bottom of the barrel 12. There may be any number of annular circumferential measuring grooves in the plunger 20. Two such measuring grooves allow ready subdivision of the syringe contents as described below into two aliquot portions. Three annular measuring grooves allow ready subdivision of the syringe contents into three portions. Four annular measuring grooves allow ready subdivision of the syringe contents into four portions, etc. Desirably the measuring grooves are equidistantly spaced from one another and the top groove is spaced a like distance from the next groove; optionally, what would be the top groove is eliminated, the groove being replaced by contact of the bottom end of the plunger with the bottom of the barrel.

In a preferred embodiment all annular measuring grooves except for the measuring groove positioned closest to the annular ring 23 have an associated, adjacent stop-start groove of which stop-start groove 32b is exemplificative. Stop-start groove 32b corresponds to a minute amount of medication to be ejected from the syringe between the predetermined volumes of medication being measured for injection by the measuring grooves.

The distance between measuring groove 32a and stop-start groove 32b, measures the minute amount of medication ejected between sequential injections of medication portions after flame sterilization of the needle permitting a user to discard any medication that has been denatured due to said flame sterilization, without destroying the accuracy of the medication dosages. The distance between stop-start groove 32b and the next measuring groove 33a allows for injection of the next full aliquot portion. In other words, after the plunger is pushed so that a detent portion 36 of the syringe engages stop-start groove 32b the next injection dosage is measured by the volume contained between stop-start groove 32b and the next measuring groove 33a. There is no need for the measuring groove closest to the annular ring to have an associated adjacent stop-start groove as there is no denatured expellant for the first injection.

As best seen in FIG. 3, a clip portion 34 is attached to the barrel 12 proximate the flange portion 28. The clip portion 34 contains the aforementioned detent portion 36 which is resiliently engageable within the annular measuring grooves 32a and the stop-start grooves 32b of the plunger 20. The detent portion 36 may be constructed in any manner which provides the aforementioned resiliency. In one embodiment, the detent portion 36 constitutes a ball detent which is operatively connected to the clip portion 34. The ball detent has a tubular element 36a, said tubular element containing therein an elongated compression spring 36b with two ends 36c and 36d, end 36d being the end closest the plunger when the ball detent engages the annular grooves. Immediately adjacent end 36d is a ball part 36e. It is ball part 36e that actually resiliently engages within the annular grooves. The clip portion 34 is preferably a split circular band with flanged ends, said clip portion having an associated clip screw 34a which rotatably extends through clear registered holes 34b in the flanges and threadedly engages a nut 34c to hold the clip in place on the barrel. The ball detent is attached to the clip portion by a generally inverted U-shaped portion 34d. Both inverted U-shaped portion 34d and clip portion 34 are dimensioned such that both may easily be slipped into place on the syringe. The clip portion and inverted U-shaped portion are slipped onto the barrel from open end 16 and are tightened in place on said barrel using clip screw 34a.

When the detent portion 36 resiliently engages any of the annular measuring grooves 32a or any of the stop-start grooves, 32b, a click emanates which can be felt in addition to being heard. This provides both an auditory and tactile indication of the position of the plunger 20 in the barrel 12.

Figure 10:
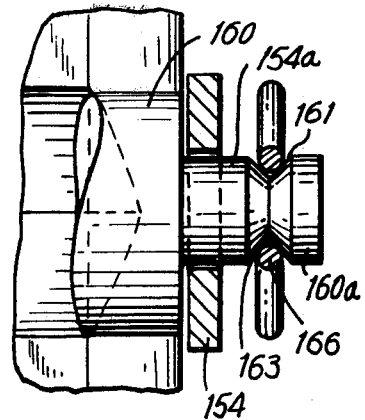
FIG. 10 is an enlarged sectional view taken substantially along line 10—10 of FIG. 9.
Figure 8:
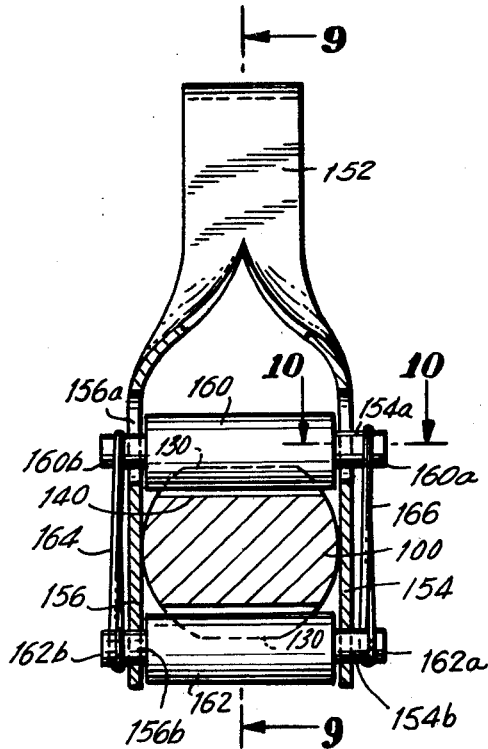
FIG. 8 is an enlarged sectional view taken substantially along line 8—8 of FIG. 7.
Figure 9:
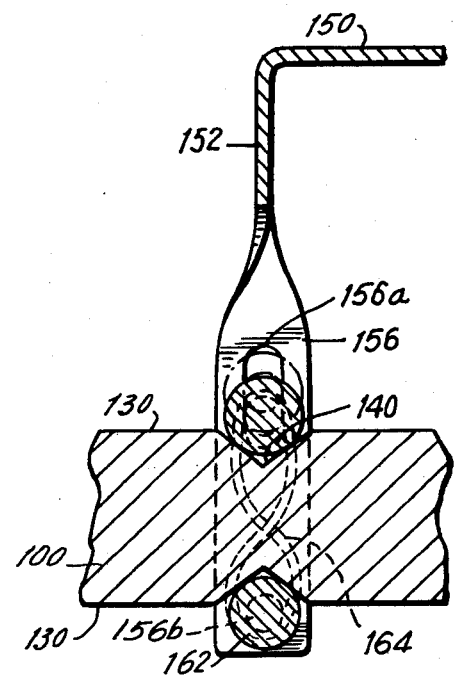
FIG. 9 is an enlarged sectional view taken substantially along line 9—9 of FIG. 8.

FIGS. 7-10 show another embodiment of a plunger 100, clip portion 110 and detent portion 120 of the present invention. In this embodiment the plunger is formed with two flat sides 130 and 130a diametrically opposite one another.

Both flat side 130 and flat side 130a are provided with either a series of transverse elongated grooves analagous in function to groove 32a or a series of transverse elongated groove pairs analagous in function to pair 32a and 32b thereon, elongated groove 140 being exemplicative of all possible grooves. The grooves on flat side 130 and the grooves on flat side 130a are formed to be diametrically opposite and in registration with one another.

Clip portion 110 includes a generally inverted U-member 150. One of the short legs 152 of U-member 150 bifurcates to form two equi-sized and dimensioned parallel U-leg extensions 154 and 156.

Each U-leg extension 154 and 156 is formed with an upper pintle receiving slot 154a and 156a and a lower pintle receiving slot 154b and 156b. The upper and lower pintle receiving slots of one U-leg extension are of the same size and shape and in registration with the upper and lower pintle receiving slots of the opposite U-leg extension. The U-leg extensions are shaped and positioned such that plunger 110 may fit between them.

Two rollers 160 and 162 are operatively supported by U-leg extensions 154 and 156 are positioned such that the plunger lies intermediate them with each flat side of the plunger having a different roller riding thereon. Each roller 160 and 162 is formed with a pair of outwardly extending registered pintles 160a and 160b. The pintles are shaped and dimensioned to rotatably fit within the slots of the U-leg extensions.

Each pintle is formed with a groove therein 161, 163 for receiving a portion of a figure-eight tension spring. Two such figure-eight springs 164, 166 are provided, spring 166 riding on the grooves of pintles 160a and 162a and spring 164 riding on the grooves of pintles 160b and 162b. The springs bias the rollers toward one another.

As the plunger 100 is moved axially lengthwise of the syringe the rollers 160 and 162 which together constitute a detent portion can either be engaged within the grooves 140 or be outside the grooves 140 dependent upon the position of the plunger. The springs are in their more relaxed state when the rollers are engaged in the grooves 140 and hence the springs cause the rollers to snappingly engage the grooves. When the rollers snappingly engage the grooves in this manner, a click emanates which can be both felt and heard, thus providing both a tactile and auditory indication of the position of plunger 100 in the barrel.

Upper roller 160 and lower roller 162 both are capable of movement into and out of the grooves 140 due to the elongation of the pintle receiving slots 154a, 154b, 156a and 156b.

Clip portion 110 is assembled on the syringe in a manner analagous to the introduction of clip portion 34 on the syringe and, hence, clip portion 110, like clip portion 34, is formed with clear registered clamping holes 168.

The above-described dual roller-bearing detent arrangement is more advantageous than the aforedescribed single ball detent arrangement due to the fact that after a long period of use the single ball detent arrangement may, due to the imbalance of pressure exerted by it, cause undue wear on other elements of the barrel and plunger. The dual roller-bearing arrangement illustrated in FIGS. 7–10 exerts a balanced pressure and hence will not cause problems even after it has been used for a long time.

As previously mentioned, the transparent barrel contains thereon visual indicia means consisting of a plurality of circumferential lines of which line 38 is a representative example and associated numerals of which numeral 40 is a representative example. Preferably the lines 38 and numbers 40 are dark in color to contrast with the light colored opaque band constituting the ray blocking means 26 against which said lines and numbers are viewed. The lines and numbers are preferably applied by silver staining. The circumferential lines 38 with their associated numerals 40 provide a visual indication of the position of the plunger 20 in the barrel 12. Any predetermined number of circumferential lines with associated numerals may be provided on the barrel 12. The appropriate number of circumferential lines and associated numbers is dependent upon the anticipated use of a particular hypodermic syringe. Thus if one is manufacturing 100 cc syringes and contemplates they will be used for two, 50 cc dosages of medication, one would provide two circumferential lines and associated numbers at the appropriate positions to indicate the two 50 cc doses. If one is manufacturing 100 cc syringes and contemplates they will be used for ten, 10 cc dosages of medication, one would provide ten circumferential lines and associated numbers properly positioned to indicate ten, 10 cc dosages on the barrel.

Each circumferential line 38 has a discontinuity 42. The discontinuity 42 provides space for the associated numerical marking 40. Preferably, the discontinuities 42 are positioned diametrically opposite the center of the ray blocking means 26. By positioning the discontinuities 42 in this manner, a user can more easily see the numerical markings 40.

In a preferred embodiment of this invention, the ray blocking means 26 extends maximally about 270° circumferentially around the barrel and ideally said ray blocking means extends about 190° circumferentially of the barrel. If the ray blocking means 26 extends more than 270° it makes it difficult to see the position of the annular ring 23 in the barrel 12.

The ray blocking means is a band having a low transmissivity to actinic light; for example: the band may constitute a metal stain to provide an amber, green or red transparent to translucent finish that has a low order of transmissivity to actinic rays. The band alternatively and preferably may be an applied layer of ceramic or glass frit. Additionally, the band of ceramic is desirably of a light color, e.g. pastel, to perform a second function, namely a contrasting background to the dark circumferential lines 38 and their associated numbers 40, thereby making the lines 38 and numbers 40 more easily read.

The syringe 10 of the present invention, when used in accordance with the method of the present invention, provides an efficient and accurate way to inoculate large numbers of people with medication that is adversely affected by actinic rays.

Normally when mass inoculations are given, a syringe that contains multiple dosages within the barrel is utilized. It is economical and expeditious to have the syringe contain enough medicament for approximately ten doses. Full syringes are laid on a surface and a battery of doctors and nurses, and/or technicians, starting with full syringes, inoculate one patient after another, flame sterilizing the hypodermic needle between patients. This type of mass inoculation is frequently practiced out of doors where the syringes are exposed to sunlight. Thus, if the medication in the syringes is labile to actinic rays, its effectiveness will be diminished.

The syringe 10 of the present invention and the method of the invention alleviate the foregoing problem.

The barrels 12 of the syringes 10 are completely filled with medication and sterile hypodermic needles 18 are fixed in place. The filled syringes 10 with the needles 18 are placed upon any appropriate flat surface. The syringes 10 are placed so that the ray blocking means 26 face in an upward direction. The user of the syringes 10 is aided in insuring that the ray blocking means 26 face upwardly by the provision of the flat portions 30 of the otherwise circular flanges 28. When the syringes 10 are placed on a flat surface, if the user lightly pushes the syringes 10, they will, due to the circularity of the flanges 30, roll until the syringes lie on the flat portions 30, thereby insuring that the ray blocking means 26 face upwardly and that the contents of the syringes are protected from the sun's actinic rays. The flats on the flanges maintain the desired position.

In this manner the contents of all the barrels 12 are protected from exposure to the sun's actinic rays without need of extra precautions, e.g. opaque sleeves, shaded cones, umbrellas, etc.

The syringe 10 of the present invention, provides the user with two distinct indications of the position of the plunger 20 in the barrel 12. This aids the user in accurately dispensing the proper amount of medication. First, utilizing the circumferential lines 38 and associated numerals 40 which contrast in color to the ray blocking means 26, the user may easily, visually read the amount of medication being dispensed. Second, when detent portion 36 of clip 34, resiliently engages each successive pair of annular grooves 32a and 32b of the plunger 20, a click emanates that can be both heard and felt, thereby providing the user with both a tactile and an auditory indication that a proper pre-selected volume of medication has been injected. The auditory and tactile indicia means is particularly useful in mass inoculations, allowing the doctors and nurses to quickly and accurately dispense multiple doses from a single syringe. Injections are facilitated and validated by the inclusion of tactile and auditory indicia means as the operator does not have to rely solely upon the visual indicia means but has the additional sensitive aids of touch and sound to help achieve the desired accuracy.

As best seen in FIG. 4, another embodiment of the hypodermic syringe of this invention can be used for safe and accurate self-injection of diabetics with insulin. Diabetics are prone to the loss of visual accuracy and need the assistance of a tactile and/or auditory signal. Insulin injecting syringe 44 is constructed similarly to syringe 10. It has a barrel 46 with two open ends 48, 50. End 50 is dimensioned to detachably receive the hub of a metal hypodermic needle 52 which is shown fixed in place in FIG. 4.

Barrel 46 contains visual indicia means comprising a series of circumferential lines 52, some of said circumferential lines with associated markings 54. The lines 52 are provided such that successive one unit integral amounts are indicated. Associated markings are associated only with certain selected lines of the circumferential lines. If associated markings were provided for all the circumferential lines it would be difficult to quickly and easily read said associated markings. Lines indicative of ten unit increments, i.e. 10, 20, 30, etc., have lines 52 which extend circumferentially almost 360° around the barrel; lines indicative of five degree unit integrals, i.e. 5, 15, 25, etc., have lines 52 extending generally 180° circumferentially around the barrel 46; lines indicative of one degree unit increments, i.e. 1, 2, 3, 4, 6, 7, etc., have lines 52 extending about 90° circumferentially around the barrel 46.

A plunger 56 is insertable into open end 48 of the barrel and mounted for sliding movement lengthwise of the barrel 46. The plunger is elongated and provided with a bottom end and annular elastomeric ring analagous to bottom end 22 with annular ring 23 of plunger 20.

Plunger 56 is further provided with a manipulative handle analagous in both structure and function to manipulative handle 24.

Plunger 56 is formed with a single annular circumferential groove 58 thereon for measuring a predetermined prescribed volume of medication between the bottom end of the plunger 56 and the bottom of the barrel. In a preferred embodiment of the invention there are ten groups of ten interchangeable plungers that can be used with syringe 44, plunger 56 being exemplicative of all possible plungers. Each plunger 56 has its single annular circumferential groove, of which groove 58 is exemplicative, in a different position, thus enabling the measurement of ten different predetermined prescribed medication volumes between the bottom end of the plunger 56 and the bottom of the barrel. The series of plunger measures discharge volume differing by 10 units for a barrel capable of holding 100 units.

Insulin injecting syringe 44 is formed with a flange portion thereon. The flange portion 60 of insulin injecting syringe 44 does not need to be formed with a single flat portion. Attached to the barrel, proximate the flange portion 60 is a clip portion 62. The clip portion is formed so that it may be in either an unlocked state wherein it is capable of axial movement lengthwise of the barrel, or a locked state wherein it is fixed in position. In a preferred embodiment, clip portion 62 is formed with a threaded set screw hole 64 therein. The set screw hole in combination with a set screw 66 which threadably fits therein, provides means for locking and unlocking the clip portion 62 to the barrel. The set screw 66 has an upper flat manipulative end 66a and a lower generally pointed tip 66b. Manipulative end 66a is formed with a slot 66c dimensioned and shaped to receive a conventional jeweler's screwdriver. The clip portion may be unlocked by backing off the set screw 66 thereby making possible the lengthwise axial movement of the clip portion along the barrel 46. The clip portion is locked by tightening the set screw. Clip portion 62 contains a detent portion which can be, by way of example, either a ball detent which is identical in structure and function to ball detent 36 of syringe 10 or two rollers with associated elements which are identical in structure and function to rollers 160 and 162 and their associated element. The clip portion is introduced onto syringe 44 in a manner identical to the manner heretofore described for introduction of clip portion 34 and detent portion 36 onto syringe 10. The clip portion 62 is formed with a reading means 68 thereon.

The barrel 46 is formed with a fine adjustment means 70 thereon. The fine adjustment means 70 consists of a series of divisional means 72 and a series of divisional lines 74, said lines formed by the edges of the divisional means. In a preferred embodiment the divisional means consists of a series of annular divisional grooves, of which divisional groove 72 is exemplicative. The divisional grooves are dimensioned and shaped to receive the lower, generally pointed tip 66b of set screw 66. Grooves 72, with associated lines 74 formed by the groove edges, indicate one unit increments. Lines 74 in a combination with reading means 68 allow a user to visually ascertain the position of the detent portion on the fine adjustment means 70. The divisional lines 74 of the fine adjustment means 70 in conjunction with the clip portion 62 are usable to make fine adjustments in the predetermined prescribed volume of medication measured when the detent portion 36 engages the annular groove 58. The fine adjustment means preferably contains thereon a numerical indicia 75 of the 0, or no change position.

A physician, or other health professional, determines the proper dosage of insulin needed by the diabetic and then chooses the appropriate plunger to be used so that the diabetic may properly self-inject said proper dosage. The appropriate plunger is the plunger having its annular groove 58 positioned so that the amount of medication dispensed when the detent portion engages said groove most closely approximates the predetermined prescribed amount of medication. In the event that said proper dosage is not a full increment of 10 units, as measured by the appropriate plunger, the doctor or other health professional proceeds to make whatever fine adjustment is needed.

In its unadjusted state, the reading means 68 of the clip portion 62 is set on the divisional line 74 indicating no change that causes the detent portion to engage the groove 58 so as to measure the precise amount of medication that would be measured by said plunger in the absence of any fine adjustment. For example, if the plunger being used measures 50 units, the reading means 68, in its unadjusted state, is set on the divisional line indicating 0, or no adjustment. If said plunger is used unadjusted, 50 units will be measured when the detent portion engages the groove.

To adjust the clip portion so that the dosage which will be self-injected is greater or less than the amount measured by the plunger, the doctor or health professional backs off the set screw 66 and moves the clip portion either upwardly or downwardly lengthwise of the barrel until the reading means 68 is in line with the divisional line indicating the incremental adjustment he desires to make. When said reading means is in proper alignment with said divisional line, the tip of the set screw 66b should be directly over a divisional groove 72 so that the physician or health professional can tighten the set screw into the divisional groove 72 thereby locking the clip portion in place. For example, if the plunger that measures 50 units is being used, the physician or other health professional may make the following adjustments: the physician or other health professional may set the clip so that the diabetic will self-inject 51 units by moving the clip portion upwardly until the reading means is in line with the divisional line which indicates a +1 increment; the physician or other health professional may set the clip so that the diabetic will self-inject 52 units by moving the clip portion upwardly until the reading means is in line with the divisional marking which indicates a +2 increment; the physician or other health professional may set the clip so that the diabetic will self-inject 53 units by moving the clip portion upwardly until the reading means is in line with the divisional line which indicates a +3 increment; the physician or other health professional may set the clip so that the diabetic will self-inject 54 units by moving the clip portion upwardly until the reading means is in line with the divisional line which indicates a +4 increment; the physician or other health professional may set the clip so that the diabetic will self-inject 49 units by moving the clip portion downwardly until the reading means is in line with the divisional line indicating a −1 unit increment; the physician or other health professional may set the clip so that the diabetic will self-inject 48 units by moving the clip portion downwardly until the reading means is in line with the divisional line indicating a −2 unit increment; the physician or other health professional may set the clip so that the diabetic will self-inject 47 units by moving the clip portion downwardly until the reading means is in line with the divisional line indicating a −3 unit increment; the physician or other health professional may set the clip so that the diabetic will self-inject 46 units by moving the clip portion downwardly until the reading means is in line with the divisional line indicating a −4 unit increment; the physician or other health professional may set the clip so that the diabetic will self-inject 45 units by moving the clip portion downwardly until the reading means is in line with the divisional line indicating a −5 unit increment. Although only the adjustments possible with the plunger which measures 50 units have been detailed, it is to be understood that all plungers of the group of plungers may be adjusted in an analagous manner. In this way, fine adjustment of the volume of medication being measured when the detent portion engages the annular groove can be made by the physician or other appropriate health professional so as to permit accurate and precise self-injection of the exact predetermined prescribed dosage.

Alternatively, the physician or other appropriate health professional may pre-set the syringe and appropriate plunger to indicate the predetermined prescribed dosage without the use of the reading means and divisional lines of the fine adjustment means. To so do, the physician or other health professional retracts the plunger until the leading edge of the annular elastomeric ring 23 proximate the plunger bottom end 22 is in line with the circumferential line 38 which indicates the exact dosage he is prescribing. The doctor or other health professional then unlocks the clip portion, moves it an appropriate distance in an appropriate direction, said appropriate distance and appropriate direction being that distance and that direction which will permit the detent portion to engage the annular groove such that the amount of medication being prescribed is measured. The clip is then relocked in position. In this way, the ncessary fine adjustment is made. As best seen in FIG. 4, and as heretofore described, syringe barrel 44 contains thereon enough circumferential lines to allow the doctor to finely adjust in the manner heretofore described, with an accuracy of within one unit.

Insulin injecting syringe 44 is usable in combination with vial 90. Vial 90 has a seal 92 which is air impermeable. In a preferred embodiment the seal 92 is made of rubber. Vial 90 is filled with insulin 94. Vial 90 also contains head space 86, in which there is no insulin.

Insulin injecting syringe 44, in combination with vial 90, provides a method for safe and accurate self-injection of diabetics with insulin and prevents the creation of a vacuum in vial 90. The user retracts the plunger 56 of an empty syringe in the ambient air until the detent portion 36 engages in the annular circumferential groove 58 of the plunger 56. This action aspirates air into the syringe 44. The user then thrusts the needle 52 through the air impervious seal 92 into the vial 90. Next, the user completely depresses the plunger 56 thereby pumping air into the vial 90 and raising the pressure of the air within said vial. This, although air is not sterile, is an acceptable aseptic technique as the insulin solution has a self-sterilizing component (preservative). The user then positions the needle tip in the insulin 44 and retracts the plunger 56 until the detent portion again engages annular groove 58, thereby aspirating the predetermined volume of insulin into the syringe. The user then injects the insulin into himself or another.

As in syringe 10, detent portion 36 and groove 58 provide an auditory and tactile indication of the position of the plunger within the syringe and thereby allow the user to accurately and easily aspirate and inject the proper amount of medication. This is particularly useful with diabetics who must inoculate themselves with insulin and who often-times have failing vision.

By following the procedure outlined above, the insulin may be drawn out of the vial 90 without creating a vacuum in said vial. If one did not pump air into the vial 90 thereby raising the air pressure within, as more and more insulin was drawn out of the vial 90 and the air pressure within the vial 90 would lower until an unacceptable degree of vacuum was created. This lowering of air pressure which eventually results in the creation of too great a vacuum, makes it increasingly difficult for the user to draw the insulin out of the vial 90 and into the insulin injecting syringe 44. This problem is avoided by the method of the present invention.

It will be understood that each of the elements described above, or two or more together, may also find a useful application in other types of constructions differing from the types described above.

While the invention has been illustrated and described as embodied in a syringe with actinic ray blocking stripe, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims.

I claim:

1. A hypodermic syringe comprising:
   (a) a transparent barrel adapted to contain a liquid medication adversely affected by actinic rays, the barrel having two open ends, one of said two ends capable of having a hypodermic needle attached thereto;
   (b) a plunger slidably insertable into the other open end of the barrel, said plunger having a bottom end with a reading means proximate thereto, and a top manipulative handle projecting beyond said one end of said barrel;

(c) visual indicia means on the barrel;

(d) non-removable, rectilinear means integral with the barrel for blocking actinic rays, said means extending generally the full length of the indicia marked portion of the barrel and between 150° and 270° circumferentially of the barrel, whereby the medication in the syringe is permanently protected from the destructive effects of actinic rays as long as said rectilinear means is uppermost, and (e) means for constantly orienting the means for blocking actinic rays upwardly from a surface upon which the syringe rests.

2. The hypodermic syringe of claim 1, wherein the barrel contains a liquid medication adversely affected by actinic rays.

3. The hypodermic syringe of claim 1, wherein the syringe further comprises:

(a) a circular flange portion which is an integral part of the barrel, said flange portion extending outwardly of the barrel;

(b) the plunger having at least one annular circumferential groove, the groove indicating a predetermined volume of medication between the bottom end of the plunger and the bottom end of the barrel; and (c) a clip portion firmly fixed to the barrel proximate the flange portion, the clip portion having a detent portion resiliently engageable with the groove of the plunger to provide an auditory and tactile indication of the position of the plunger.

4. The hypodermic syringe of claim 3, wherein the needle can be flame sterilized and wherein all of the annular grooves except the annular groove closest the bottom end of the plunger have an associated, adjacent stop-start groove for allowing ejection of minute amounts of medication.

5. The hypodermic syringe of claim 1, wherein the orienting means consists of a single flat portion on the barrel flange, said flat portion so positioned to be diametrically opposite the transverse center of the ray blocking means.

6. The hypodermic syringe of claim 1, wherein the means for blocking out rays consists of a light colored band with a low transmissivity to actinic rays.

7. The hypodermic syringe of claim 6, wherein the band is ceramic or opaque glass frit baked on the syringe barrel.

8. The hypodermic syringe of claim 6, wherein the band is a metal stain with a transparent to translucent finish.

9. The hypodermic syringe of claim 6, wherein the visual indicia is a color contrasting to the color of the means for blocking actinic rays.

10. The hypodermic syringe of claim 1, wherein the visual indicia means consists of a plurality of circumferential lines, each of said lines having a discontinuity diametrically opposite the center of the means for blocking actinic rays so as to provide a space for numerical markings indicating successive aliquot portions.

11. A method of inoculating large numbers of people utilizing the hypodermic syringe of claim 1, wherein a plurality of such syringes are filled with medication, said syringes being used in conjunction with a sterilizable hypodermic needle, the method comprising the steps of:

(a) placing the plurality of filled syringes with the needles in place, on a flat surface, in a manner such that the means for blocking actinic rays faces uppermost;

(b) inoculating a person utilizing one of the plurality of hypodermic syringes and its associated needle;

(c) resterilizing the hypodermic needle;

(d) ejecting any impaired medication from the needle;

(e) inoculating a second person utilizing the same one hypodermic syringe;

(f) continuing steps (b) through (e) seriatim until all of the medication in the syringe has been used;

(g) inoculating another person with a different one of the plurality of syringes and its associated sterilized needle;

(h) performing steps (d) through (f) seriatim until all the medication in the different one of the plurality of hypodermic syringes has been used; and (i) continuing steps (g) and (h) with different pre-loaded hypodermic syringes until all of the people have been inoculated or all of the filled syringes used.

12. The method of claim 11, wherein the barrel has an annular flange and the steps of placing the syringe on a flat surface such that the means for blocking actinic rays faces uppermost is performed by forming a flattened surface on the flange opposite the ray blocking means, and, if necessary, manually urging the syringe to lie on its flattened surface.

13. In combination:

(a) a hypodermic syringe barrel having two open ends, one of said ends capable of receiving a sterile hypodermic needle, said barrel having a flange portion integral therewith;

(b) visual indicia means on the barrel;

(c) a group of plungers, each plunger of the group insertable into the other open end of the barrel, each plunger of the group having a bottom end with a plunger reading means proximate thereto, and a top manipulative handle, each plunger of the group also having one annular circumferential groove corresponding to a predetermined volume of medication between the bottom end of the plunger and the bottom end of the barrel;

(d) fine adjustment means on the barrel, said fine adjustment means being situated generally proximate said flange, said fine adjustment means comprising a series of divisional lines and annular divisional grooves, said lines formed by the edges of said grooves; and (e) a clip portion firmly attached to the barrel proximate the flange portion and having a detent portion resiliently engageable with the groove of each of the plungers of the group to provide an auditory and tactile indication of the position of the plunger in the barrel, said clip portion having a locking means for allowing the clip portion to be in an unlocked state in which it is movable lengthwise of the barrel or a locked state in which it is fixed in a pre-set position on the barrel, said clip portion also having clip reading means thereon, the reading means in combination with the divisional lines of the fine adjustment means capable of indicating the position of the detent portion on the barrel.

14. The combination of claim 13, wherein the locking means comprises a set screw hole formed in the clip portion together with a set screw, said set screw unlocking the clip portion when backed off and locking the clip portion when tightened.

15. The combination of claim 13, wherein the group of plungers consists of several plungers, and in which the series of divisional lines consists of a number of divisional lines, one greater than the number of plungers.

16. A method of adjustingly pre-setting the combination of claim 13 so that a predetermined prescribed dosage of insulin can be accurately measured and self-injected by a diabetic, said method comprising the steps of:
   (a) determining a correct dosage of insulin to be self-injected by the diabetic; and
   (b) choosing an appropriate plunger from the group of plungers, said appropriate plunger being the plunger of the group having its annular circumferential groove positioned such that when it is engaged by the detent portion the dosage amount measured is approximate in unit numbers the predetermined prescribed dosage.

17. The method of claim 16, and additionally comprising the step of finely adjusting the combination to permit the detent portion to engage the annular groove such that an exact predetermined prescribed dosage is measured.

18. The method of claim 17, wherein the step of finely adjusting the combination is done by retracting the plunger until the reading means of the plunger is in line with an appropriate visual indicia means, the appropriate visual indicia means indicating the exact predetermined prescribed dosage and then unlocking the clip portion and moving it an appropriate distance in an appropriate direction, said appropriate distance and said appropriate direction being the distance and direction permitting the detent portion to engage the annular groove such that the exact predetermined prescribed dosage will be measured, and relocking the clip portion thereby fixedly adjusting the combination to measure said exact predetermined prescribed amount of medication when the detent portion engages the annular groove.

19. The method of claim 18, wherein the step of finely adjusting the combination is done by unlocking the clip portion and moving same an appropriate distance in an appropriate direction, said appropriate distance and said appropriate direction being located by placing the reading means of the clip in line with a pre-chosen division line, said pre-chosen division line being the line indicating an amount which when added to or subtracted from the dosage measured by the plunger equals the exact predetermined prescribed dosage, and relocking the clip portion thereby fixedly adjusting the combination such that the exact predetermined prescribed dosage will be measured when the detent portion engages the annular groove.

20. A hypodermic syringe as set forth in claim 1, wherein the rectilinear means is selected from the group consisting of baked glass frit and metallic stain.

21. A hypodermic syringe comprising:
   (a) a transparent barrel adapted to contain a liquid medicament, the barrel having two open ends, one of said two ends capable of having a hypodermic needle attached thereto;
   (b) a plunger insertable into the other open end of the barrel, said plunger having a bottom end and a top manipulative handle;
   (c) visual indicia means on the barrel;
   (d) the plunger having at least one annular circumferential measuring groove, the measuring groove indicating a predetermined volume of medication between the bottom end of the plunger and the bottom end of the barrel;
   (e) a clip firmly fixed to the barrel proximate the other open end;
   (f) a detent carried by the clip and resiliently engageable with the measuring groove of the plunger to provide an auditory and tactile indication of the position of the plunger when the plunger reaches a position such that the detent is in the measuring groove;
   (g) wherein the needle can be flame sterilized; and
   (h) the measuring groove has associated therewith stop/start groove for allowing ejection of a minute amount of medication as the plunger travels the distance between said measuring groove and said stop/start grooves.

* * * * *